US009925523B2

(12) United States Patent
Baik et al.

(10) Patent No.: US 9,925,523 B2
(45) Date of Patent: Mar. 27, 2018

(54) SELF-POWERED PIEZOELECTRIC STRUCTURE AND METHOD OF MANUFACTURING THE SAME

(71) Applicant: Industry-Academic Cooperation Foundation, Yonsei University, Seoul (KR)

(72) Inventors: Hong Koo Baik, Seoul (KR); Woo Soon Jang, Seoul (KR); Sun Woong Han, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 496 days.

(21) Appl. No.: 14/578,649

(22) Filed: Dec. 22, 2014

(65) Prior Publication Data

US 2015/0182652 A1    Jul. 2, 2015

(30) Foreign Application Priority Data

Dec. 31, 2013  (KR) .......................... 10-2013-168287

(51) Int. Cl.
| | | |
|---|---|---|
| B01J 23/06 | (2006.01) | |
| B01J 31/24 | (2006.01) | |
| B01J 31/02 | (2006.01) | |
| B01J 35/00 | (2006.01) | |
| B01J 37/34 | (2006.01) | |
| B01J 37/02 | (2006.01) | |
| B01J 27/051 | (2006.01) | |
| C02F 1/72 | (2006.01) | |
| H01L 41/113 | (2006.01) | |
| H01L 41/18 | (2006.01) | |
| H01L 41/317 | (2013.01) | |
| B01J 21/06 | (2006.01) | |
| C02F 101/30 | (2006.01) | |

(52) U.S. Cl.
CPC ............. *B01J 23/06* (2013.01); *B01J 21/063* (2013.01); *B01J 27/051* (2013.01); *B01J 31/0237* (2013.01); *B01J 31/24* (2013.01); *B01J 31/2404* (2013.01); *B01J 31/2409* (2013.01); *B01J 35/004* (2013.01); *B01J 35/0033* (2013.01); *B01J 37/0219* (2013.01); *B01J 37/345* (2013.01); *B01J 37/349* (2013.01); *C02F 1/725* (2013.01); *H01L 41/1136* (2013.01); *H01L 41/183* (2013.01); *H01L 41/317* (2013.01); *A61L 2209/132* (2013.01); *B01J 2231/321* (2013.01); *C02F 2101/30* (2013.01); *C02F 2201/009* (2013.01); *C02F 2305/10* (2013.01); *Y02A 20/212* (2018.01)

(58) Field of Classification Search
None
See application file for complete search history.

(56) References Cited

U.S. PATENT DOCUMENTS

| | | | | |
|---|---|---|---|---|
| 4,483,756 A * | 11/1984 | Lowther | ................ | B01J 8/02 204/155 |
| 8,003,982 B2 * | 8/2011 | Wang | ................ | H02N 2/18 257/43 |
| 8,072,122 B2 * | 12/2011 | Gao | ................ | H02N 2/183 310/330 |
| 8,664,833 B2 * | 3/2014 | Ko | ................ | B60C 23/0411 310/321 |
| 9,024,510 B1 * | 5/2015 | Chen | ................ | H01L 41/0478 310/339 |
| 9,099,310 B1 * | 8/2015 | Lee | ................ | H01L 21/02381 |
| 9,196,820 B2 * | 11/2015 | Benwadih | ................ | G01L 9/008 |
| 2008/0283751 A1 * | 11/2008 | Kymissis | ................ | G01J 5/34 250/338.3 |
| 2009/0039014 A1 * | 2/2009 | Katsurao | ................ | B01D 67/0074 210/500.23 |
| 2011/0143924 A1 * | 6/2011 | Hisata | ................ | C09D 5/1618 502/159 |
| 2011/0217519 A1 * | 9/2011 | Sakashita | ................ | B32B 9/00 428/172 |
| 2012/0049692 A1 * | 3/2012 | Boyd | ................ | E01C 7/18 310/319 |
| 2013/0334930 A1 * | 12/2013 | Kang | ................ | H01L 41/113 310/339 |

FOREIGN PATENT DOCUMENTS

| | | |
|---|---|---|
| JP | 2011-181866 | 9/2011 |
| JP | 2013-026619 | 2/2013 |
| KR | 10-2004-0015928 | 2/2004 |
| KR | 10-2007-0027098 | 3/2007 |
| KR | 10-2009-0025409 | 3/2009 |
| KR | 10-20130-0055867 | 5/2013 |
| KR | 10-2013-0139603 | 12/2013 |

OTHER PUBLICATIONS

Zhu et al. "Flexible High-Output Nanogenerator Based on Lateral ZnO Nanowire Array", Nano Lett. 2010,10,3151-3155.*
Kumar et al. "Recent advances in power generation through piezoelectric nanogenerators", Journal of Materials Chemistry, 2011,21,18946-18958.*

* cited by examiner

Primary Examiner — Nicole M Buie-Hatcher

(57) ABSTRACT

According to an illustrative embodiment of the present invention, a self-powered piezoelectric structure is provided which includes a base material that can be bent by an externally applied force, and a catalyst layer formed on the base material, wherein the catalyst layer is formed by using a mixture of a catalytic material, which can be activated when the energy is applied thereto from an outside, and a piezoelectric material.

16 Claims, 4 Drawing Sheets

SELF-POWERED PIEZOELECTRIC STRUCTURE AND METHOD OF MANUFACTURING THE SAME

CROSS REFERENCE TO RELATED APPLICATION

The present application claims priority from Korean Patent Application Number 10-2013-168287 filed on Dec. 31, 2013, the entire contents of which are incorporated herein for all purposes by this reference.

BACKGROUND OF THE INVENTION

Field of the Invention

The present invention relates to a piezoelectric structure, and more particularly, to a piezoelectric structure configured to remove (decompose) organic matters in water, for example, by using catalyst, which is activated using light, electrical energy and the like, such as photocatalyst, electrochemical catalyst and the like, and a method of manufacturing the same.

Description of Related Art

Photocatalyst that is activated by light has been widely known.

The photocatalyst generates therein electrons and holes by using the light and decomposes water into hydroxide (—OH) and proton (H+) by using the same. By the oxidation/reduction process of the water, it is possible to decompose the organic matters in the water, for example. Thus, the photocatalyst has been diversely used in many fields (for example, refer to Korean Patent Application Publication No. 10-2004-15928).

According to the above technology, a light illumination lamp is provided in a reactive tank, the light is illuminated to the photocatalyst and incoming water to remove the organic matters from the incoming water through the photocatalyst. However, in order to activate the photocatalyst, an illumination means such as the light illumination lamp should be used. Like this, since the photocatalyst requires the light energy, it cannot be used in an environment in which a separate illumination means cannot be provided because the depth of water is deep, and a space where the light is shielded.

The information disclosed in the Background of the Invention section is provided only for better understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide a self-powered piezoelectric structure having a means capable of activating photocatalyst, which is activated by illuminating light, without illuminating the light and a method of manufacturing the same.

Also provided are a self-powered piezoelectric structure configured to activate the photocatalyst even without illuminating the light thereto and to remove (decompose) organic matters and the like and a method of manufacturing the same.

Also provided are a self-powered piezoelectric structure having a means capable of activating not only the photocatalyst but also a catalytic material, which is activated by applying the energy from an outside, such as electrochemical catalyst, even though a separate external energy source is not provided, and a method of manufacturing the same.

In an aspect of the present invention, there is provided a self-powered piezoelectric structure for inducing a predetermined catalytic reaction. The structure includes a base material that can be bent by an externally applied force, and a catalyst layer formed on the base material, wherein the catalyst layer is formed by using a mixture of a catalytic material, which can be activated when the energy is applied thereto from an outside, and a piezoelectric material, wherein at least a part of the catalytic material in the catalyst layer is exposed to the outside, and wherein the self-powered piezoelectric structure is configured so that when a force is externally applied to the base material, the catalytic material in the catalyst layer is activated by a potential generated from the piezoelectric material in the catalyst layer and the catalytic reaction is thus induced, even at an environment where light is shielded.

According to an illustrative embodiment, a photocatalyst, an electrochemical catalyst or thermal catalyst may be used as the catalytic material.

According to an illustrative embodiment, at least a part of the catalytic material in the catalyst layer may be exposed to the outside by a plasma treatment for the catalyst layer.

According to an illustrative embodiment, at least one of $TiO_2$, ZnO and $MoS_2$ may be used as the catalytic material.

According to an illustrative embodiment, a polymer piezoelectric material may be used as the piezoelectric material.

According to an illustrative embodiment, PVDF-TrFE (polyvinyledenedifluoride-tetrafluoroethylene) may be used as the piezoelectric material.

According to an illustrative embodiment, the catalyst layer may be formed on both surfaces of the base material.

According to an illustrative embodiment, the self-powered piezoelectric structure may be used for decomposing organic materials in water.

In another aspect of the present invention, there is provided a method of manufacturing a self-powered piezoelectric structure for inducing a predetermined catalytic reaction. The method includes the steps of providing a base material that can be bent by an externally applied force; forming a catalyst layer formed on the base material by using a mixture of a catalytic material, which can be activated when the energy is applied thereto from an outside, and a piezoelectric material, and exposing at least a part of the catalytic material in the catalyst layer to the outside, wherein the self-powered piezoelectric structure is configured so that when a force is externally applied to the base material, the catalytic material in the catalyst layer is activated by a potential generated from the piezoelectric material in the catalyst layer and the catalytic reaction is thus induced, even at an environment where light is shielded.

According to an illustrative embodiment of the method, a photocatalyst, an electrochemical catalyst or thermal catalyst may be used as the catalytic material.

According to an illustrative embodiment of the method, at least a part of the catalytic material in the catalyst layer may be exposed to the outside by a plasma treatment for the catalyst layer.

According to an illustrative embodiment of the method, at least one of $TiO_2$, ZnO and $MoS_2$ may be used as the catalytic material.

According to an illustrative embodiment of the method, a polymer piezoelectric material may be used as the piezoelectric material.

According to an illustrative embodiment of the method, PVDF-TrFE (polyvinyledenedifluoride-tetrafluoroethylene) may be used as the piezoelectric material.

According to an illustrative embodiment of the method, the catalytic material and the PVDF-TrFE are mixed in an organic solvent and the catalyst layer may be formed on the base material by spin coating a mixture solution.

According to an illustrative embodiment of the method, as a ratio of the catalytic material to the piezoelectric material in the catalyst layer increases, contact sites of water molecules or organic matters with the catalyst layer increases.

According to an illustrative embodiment of the method, the catalyst layer may be formed on both surfaces of the base material.

In still another aspect of the present invention, there is provided a self-powered piezoelectric structure for inducing a predetermined catalytic reaction. The structure is configured to be bent by an externally applied force. The self-powered piezoelectric structure is formed using a mixture of a catalytic material, which can be activated when the energy is applied thereto from an outside, and a piezoelectric material. At least a part of the catalytic material in the self-powered piezoelectric structure is exposed to the outside. The self-powered piezoelectric structure is configured so that when a force is externally applied to the self-powered piezoelectric structure, the catalytic material is activated by a potential generated from the piezoelectric material and the catalytic reaction is thus induced, even at an environment where light is shielded.

According to an illustrative embodiment, a photocatalyst, an electrochemical catalyst or thermal catalyst may be used as the catalytic material.

According to an illustrative embodiment, the self-powered piezoelectric structure may be provided in a film, fiber or pillar shape.

As set forth above, the self-powered piezoelectric structure can activate the catalytic material by the external mechanical force even when the light is not illuminated thereto. That is, the piezoelectric material generates the piezoelectric potential by the external mechanical force, and the piezoelectric potential can activate the catalytic material. Therefore, it is possible to utilize the piezoelectric structure of the present invention in a deep-water environment, an environment where the light is shielded, an environment where even when there is the light, an amount of the light is not sufficient to activate the catalyst (for example, photocatalyst), and the like. In particular, the piezoelectric structure of the present invention can be used as a use for removing the organic matters in water, without any particular limitation and without special additive means (for example, a light source).

The structures and methods of the present invention have other features and advantages which will be apparent from, or are set forth in greater detail in the accompanying drawings, which are incorporated herein, and in the following Detailed Description of the Invention, which together serve to explain certain principles of the present invention.

BRIEF DESCRIPTION OF THE DRAWINGS

FIG. 1 illustrates a catalytic material (photocatalyst) and a piezoelectric polymer material, which are used in a process of manufacturing a self-powered piezoelectric structure (substrate) according to an illustrative embodiment of the present invention, a state where the photocatalyst material in the polymer is exposed by plasma treatment, and the like.

DETAILED DESCRIPTION OF THE INVENTION

Reference will now be made in detail to exemplary embodiments of the present invention, examples of which are illustrated in the accompanying drawings. Herein, detailed descriptions of functions and components well known in the art will be omitted. Even if such descriptions are omitted, the constructions, functions and so on of a self-powered generator according to the present invention will be apparent to a person skilled in the art from the following description.

As described in relation to the related art, the photocatalyst is a material that can be activated by illuminating the light thereto. Therefore, it is not possible to utilize the photocatalyst in a deep-water environment and a light-shielded environment. In an illustrative embodiment of the present invention, in order to overcome the limitations of the photocatalyst, a self-powered piezoelectric structure, for example, a photocatalytic substrate is disclosed which can generate the piezoelectric energy other than the light energy, as the energy capable of generating electrons and holes in a catalytic material, and thus activate the photocatalyst even when a separate external light source such as light energy and electricity is not provided In a below illustrative embodiment, $TiO_2$ was used as the photocatalytic material, a piezoelectric material capable of generating a piezoelectric potential by using small mechanical energy, which is likely to be wasted in a light-shielded environment, for example, and the photocatalytic material were combined to provide a self-powered piezoelectric structure. Also, it was confirmed whether organic matters in water could be decomposed by using the piezoelectric structure. In the below, the illustrative embodiment of the present invention will be described in more detail with reference to the drawings.

In the illustrative embodiment, a self-powered piezoelectric structure (substrate) capable of generating piezoelectric potential is provided. In order to investigate a chemical reaction thereof, a polyimide substrate was selected as a flexible substrate that can be bent by the externally applied force, and a photocatalytic layer was formed thereon. The photocatalytic layer was composed of a mixture of $TiO_2$-25 and PVDF-TrFE (polyvinyledenedifluoride-tetrafluoroethylene) (polymer piezoelectric material).

Figure 1:
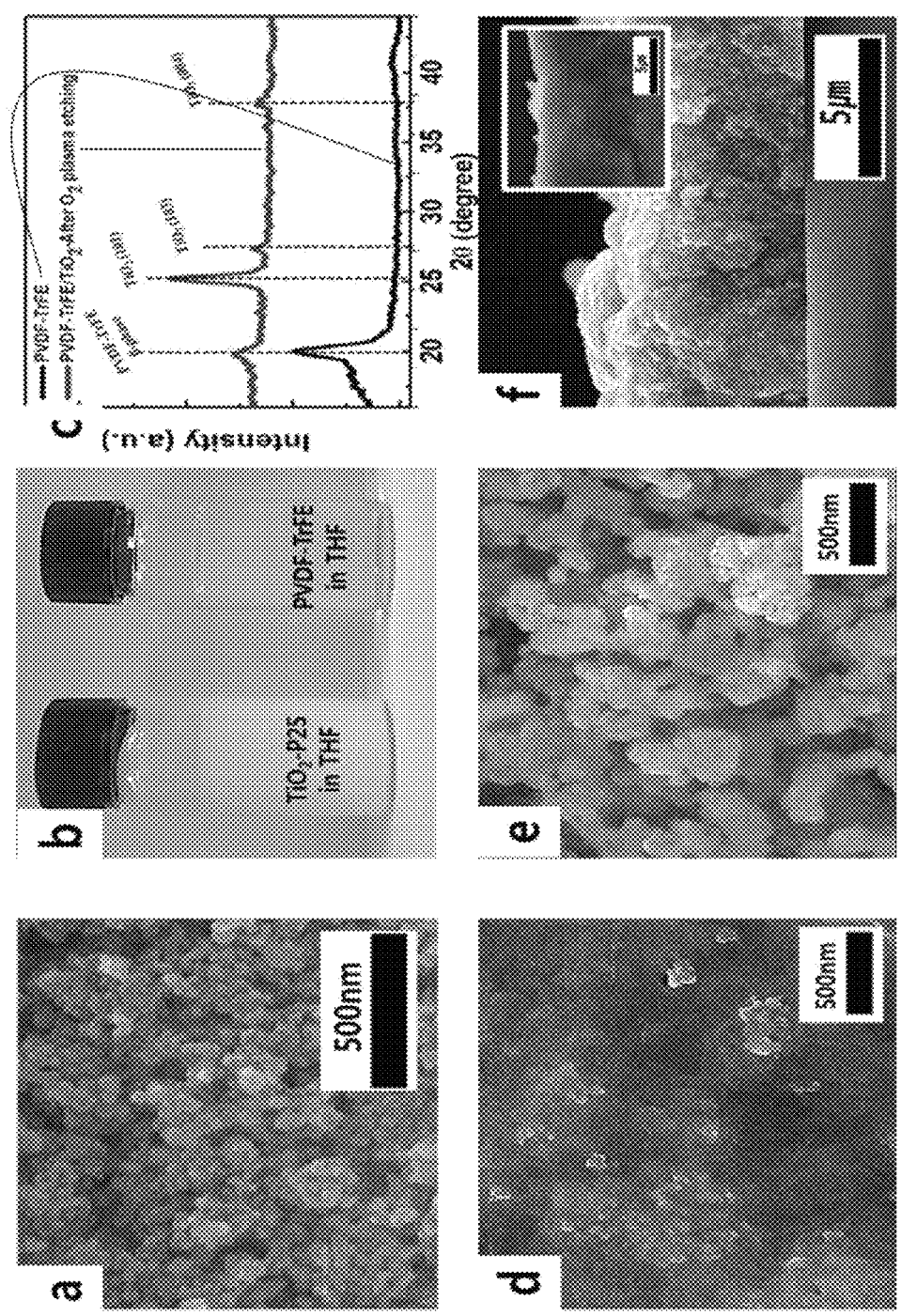

Specifically, in FIG. 1, a) is a SEM image of pristine $TiO_2$-25 as it was purchased, illustrating particle size and distribution state thereof. Then, $TiO_2$-25 and PVDF-TrFE were respectively mixed in the same organic solvent (THF (tetrahydrofuran), in this illustrative embodiment) and were completely dispersed in the solvent (refer to b) in FIG. 1). Then, a piezoelectric catalytic layer having a thickness of about 6 to 8 μm was formed on the polyimide substrate by using a spin coating method (refer to d) in FIG. 1).

In the meantime, according to a preferred illustrative embodiment, a process of exposing the photocatalyst to an outside is further performed. That is, since the photocatalyst may be bound in the PVDF-TrFE polymer, a surface of the piezoelectric catalytic layer was etched using $O_2$ plasma so as to expose the photocatalyst bound in the polymer to the outside (i.e., so as to increase an effective area of the photocatalyst). In this illustrative embodiment, the etching process was performed using the $O_2$ plasma. However, the present invention is not limited thereto. For example, an organic solvent or UV light source may also be used. Also, argon may be used upon the plasma etching, instead of the oxygen. However, according to the former method, the organic matters may remain on an inorganic surface, and according to the latter method, the efficiency is lowered, as compared to the plasma etching. Therefore, according to the preferred illustrative embodiment, the plasma, more preferably, oxygen plasma is used to perform the etching process.

In FIG. 1, $d$) and $e$) illustrate surface states of the piezoelectric catalytic layer before and after the etching using the $O_2$ plasma. By the plasma etching process, the effective area of the piezoelectric catalytic layer surface is remarkably increased (refer to $c$) in FIG. 1). In the meantime, $f$) in FIG. 1 is a SEM image of the surface of the piezoelectric catalytic layer after the etching using the $O_2$ plasma, and $c$) in FIG. 1 shows XRD results before and after the etching using the $O_2$ plasma.

Figure 2:
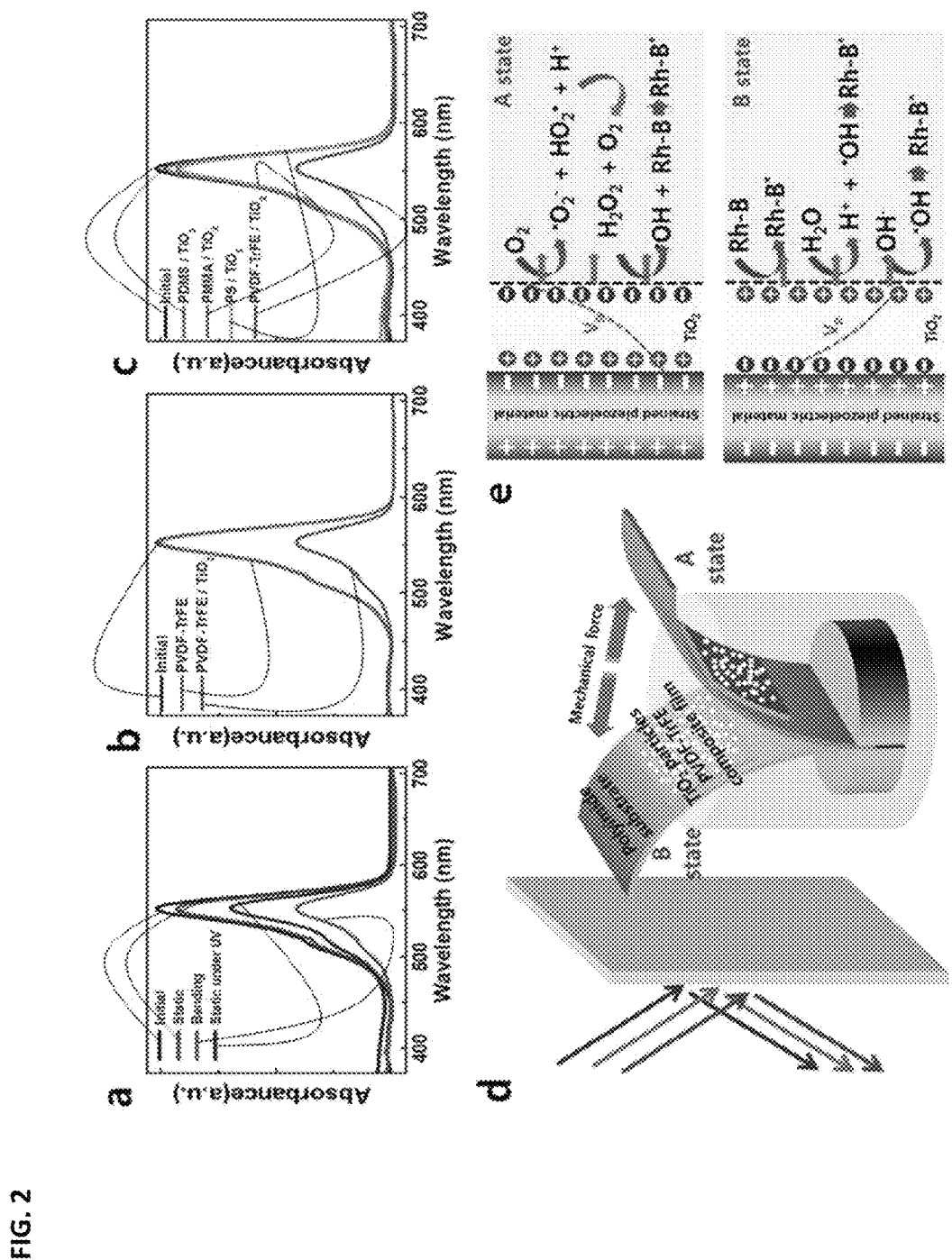
FIG. 2 illustrates a test method of using the self-powered piezoelectric structure manufactured according to the illustrative embodiment of the present invention, and efficiency of removing organic matters in water by using the piezoelectric structure.

In FIG. 2, $d$) pictorially shows a photocatalytic substrate manufactured according to the above process and a test method using the same. Test results and a reaction mechanism is shown in ($a$) to ($c$) and ($e$) of FIG. 2.

A test for investigating characteristics of the photocatalyst substrate manufactured according to the above process was performed in a space where the sunlight was shielded. Rhodamine B (tetraethylrhodamine, RhB) (a material that is frequently used in a test for checking organic matter decomposition of the catalyst) of a specific ratio was dispersed in deionized water, which was then filled in a receptacle having the substrate disposed therein. Then, a rotary motor capable of inducing mechanical deformation for the piezoelectric catalytic layer of the photocatalyst substrate was used to perform the test (refer to $d$) in FIG. 2).

In FIG. 2, $a$) shows a concentration change of RhB after the light was shielded at a stationary state, a concentration change of RhB after only the UV energy was used at a stationary state and a concentration change of RhB after the light was shielded and then the mechanical deformation was applied, respectively. As shown, it can be seen that although any catalytic reaction could not expected at the state where the light was shielded (refer to "static"), the catalytic reaction was induced when applying the UV energy and the mechanical energy. It can also be seen that when the catalytic reaction was induced for the same time (60 minutes), the catalytic reaction was more effective when the piezoelectric potential was used, as compared to the effect by the photocatalyst. The reason is as follows: an electrical double layer is formed at an interface between the piezoelectric catalytic layer and the water solution by the potential generated by the piezoelectric effect, so that an attractive force of more water molecules or organic matter molecules to the catalyst surface is more strongly applied (refer to $e$) in FIG. 2).

In FIG. 2, $b$) shows a concentration change of RhB in water depending on whether $TiO_2$—P25 is provided in the piezoelectric catalytic layer. It can be seen that the concentration change of RhB in water is higher in the piezoelectric catalytic layer including $TiO_2$—P25 therein. In FIG. 2, $c$) shows a concentration change of RhB in water depending on whether PVDF-TrFE is provided in the piezoelectric catalytic layer. It can be seen that PVDF-TrFE generates the piezoelectric potential by the mechanical deformation thereby inducing the catalytic reaction. In the meantime, $f$) in FIG. 2 pictorially shows the catalytic reaction by the compressive force and tensile force applied to the piezoelectric catalytic layer by using a simple chemical equation.

In the meantime, the inventors compared the efficiency of the manufactured photocatalyst substrate by using various test parameters. The results are shown in FIG. 3.

Figure 3:
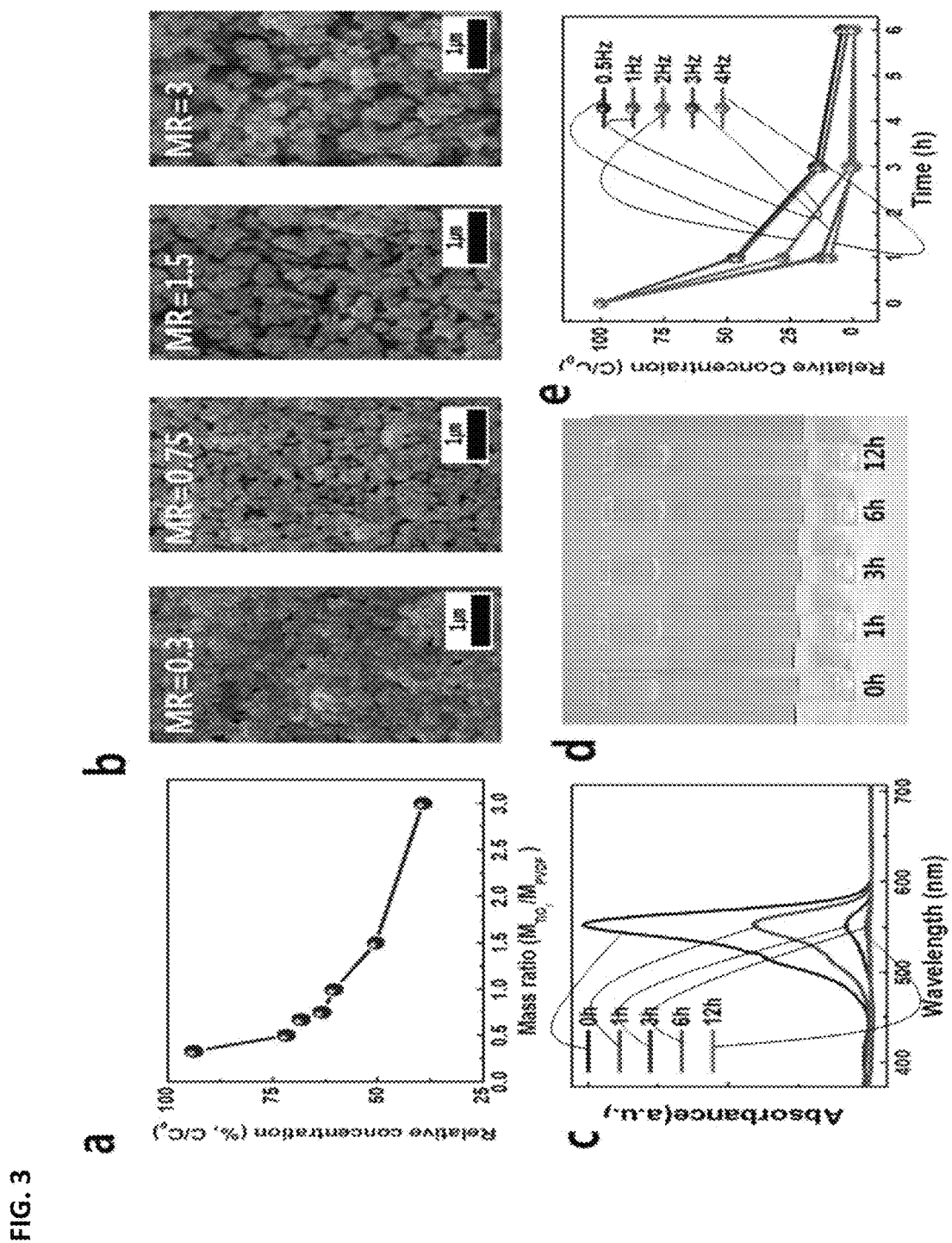
FIG. 3 illustrates decomposition efficiency of the organic matters in accordance with a mixing ratio of the photocatalyst material and the piezoelectric material.

In FIG. 3, $a$) and $b$) show surface changes of the piezoelectric catalytic layer and decomposition characteristics of RhB as a mixing ratio of $TiO_2$—P25 and PVDF-TrFE is changed. That is, when a relative ratio of $TiO_2$—P25 was increased, the surface roughness was relatively increased after the etching using the $O_2$ plasma (refer to $b$) in FIG. 3). As a result, a number of active sites at which the water molecules or organic matters in water (RhB) can directly or indirectly contact the piezoelectric catalytic layer and can be thus reacted was increased. Therefore, it can be seen that it is more efficient to increase the relative ratio of $TiO_2$—P25, which is a catalytic material, as compared to an increase in the ratio of PVDF-TrFE generating the piezoelectric potential, so as to increase the operational effect of the photocatalyst in the piezoelectric catalytic layer.

In FIG. 3, $c$) shows a concentration change of RhB in water over time at a condition where the relative mixing ratio of $TiO_2$—P25 and PVDF-TrFE was 3. It can be seen that RhB was more decomposed over time. In FIG. 3, $d$) visually shows the result of $c$) through a digital image.

The inventors also observed a concentration change of RhB as a period of applying the mechanical deformation was changed for the same test group (refer to $e$) in FIG. 3). As shown, when the period of applying the mechanical deformation was increased for the same time, the organic matters were decomposed more efficiently.

Figure 4:
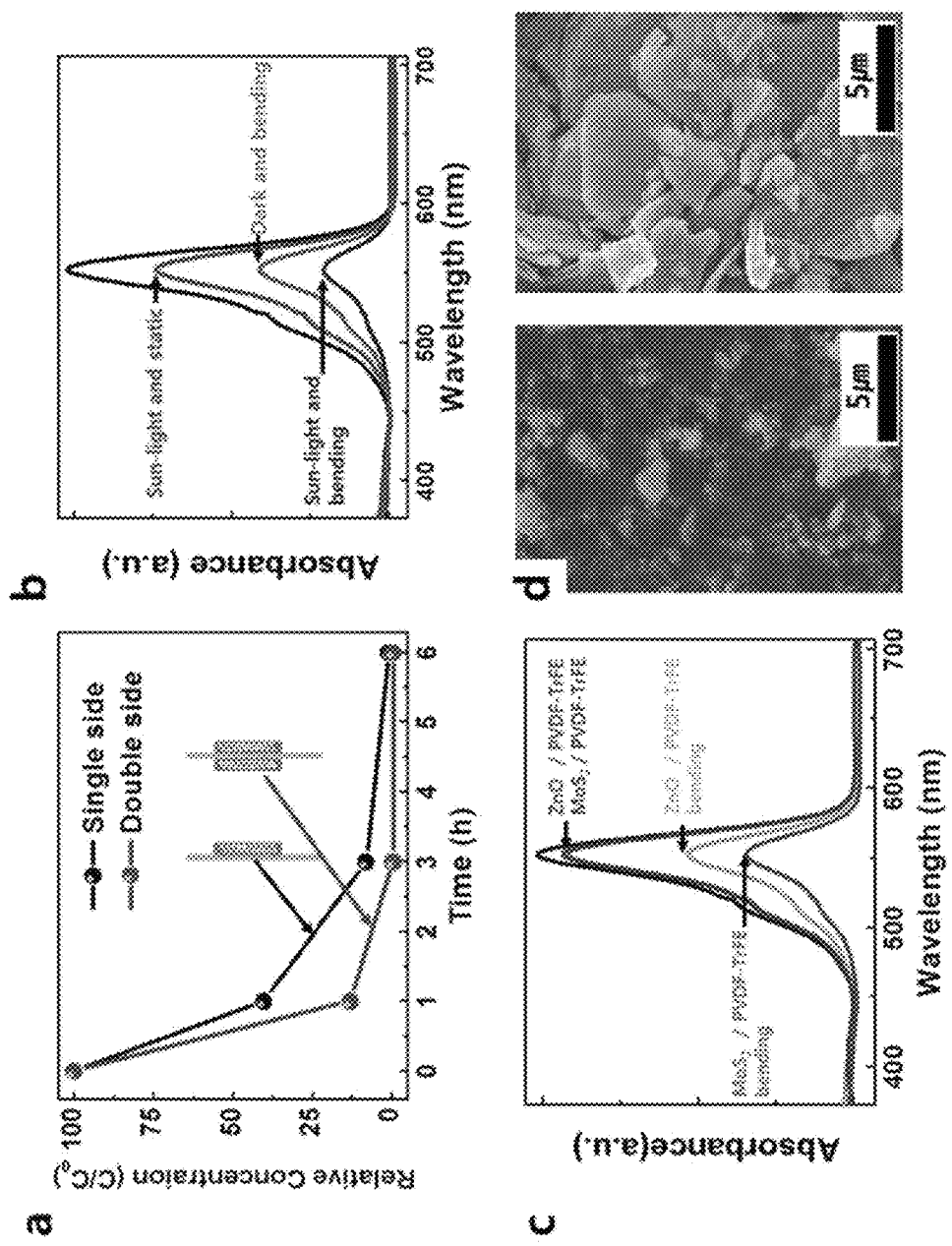
FIG. 4 illustrates a method of improving the organic matter removing efficiency of the substrate and organic matter removing results by using photocatalyst material other than $TiO_2$.

In FIG. 4, $a$) shows the organic matter removing efficiency when the piezoelectric catalytic layer was formed on one surface of the substrate and when the piezoelectric catalytic layer was formed on both surfaces of the substrate. As shown, when the piezoelectric catalytic layer was formed on both surfaces of the substrate, the organic matter removing efficiency in water was increase over time, as compared to when the organic matter removing efficiency was formed only one surface of the substrate.

In FIG. 4, $b$) shows the organic matter decomposition efficiency when the substrate was used at various conditions. It can be seen that when the substrate was applied with the mechanical deformation at an environment where the light energy was applied, the efficiency was increased.

In FIG. 4, $c$) shows the organic matter decomposition efficiency when ZnO and $MoS_2$ were used instead of $TIO_2$, as the catalytic material. As shows, the catalytic materials also have the organic matter decomposition effect. That is, it is possible to appropriately configure a piezoelectric catalytic layer depending on a surrounding environment and a type of a material to be decomposed. This means that a utilization possibility of the substrate of the present invention can be enlarged. In the meantime, $d$) in FIG. 4 shows states after ZnO and $MoS_2$ were mixed with PVDF-TrFE and then the plasma etching process was performed.

Although the present invention has been described with reference to the illustrative embodiment, it should be noted that the present invention is not limited thereto.

For example, in the above illustrative embodiment, the polyimide substrate has been exemplified as the substrate.

However, any substrate composed of a material having flexibility that can be bent by the external mechanical force can be also used, in addition to the polyimide substrate. Also, in the above illustrative embodiment, the substrate has been exemplified. However, the substrate should be construed in a broad sense. That is, although a substrate may be a flat flexible substrate as described in the above illustrative embodiment, the substrate may have a fiber or pillar shape. Therefore, the present invention is not limited to a specific shape of the substrate. That is, the present invention is not particularly limited to a specific shape and material of the substrate inasmuch as a material of the substrate can carry thereon a catalytic layer and can be bent by an externally applied force. Therefore, the substrate of the present can also be referred to as a base material. Also, the substrate (base material) may be omitted in some illustrative embodiments. That is, when the piezoelectric material such as PVDF-TrFE is provided in a flexible film form, a separate substrate (base material) for carrying thereon the catalytic layer may be omitted.

Also, in the above illustrative embodiment, the PVDF-TrFE polymer has been exemplified. However, any piezoelectric material capable of applying a piezoelectric potential to the photocatalyst may also be used, instead of the polymer. Also, the piezoelectric catalytic layer was formed on the substrate by using the spin coating. However, the present invention is not limited to the spin coating. For example, when the present invention is implemented as a film shape, a drop casting, a silk screen and the like may be adopted. Also, when the present invention is implemented as a fiber form, a spinning method, an electrospinning method and the like may be adopted.

Also, in the above illustrative embodiment, $TiO_2$ has been exemplified. However, $TiO_2$ can be used not only as the photocatalyst but also as the electrochemical catalyst. Therefore, the present invention is not limited to the catalyst having a specific use. In addition to the photocatalyst, the thermal catalyst, the electrochemical catalyst and the like are materials that can be activated by applying the energy from the outside, and the present invention can also be applied to the corresponding materials. For example, $TiO_2$ and $MoS_2$ are materials that are used not only as the photocatalyst but also as the electrochemical catalyst.

As set forth above, the illustrative embodiments can be made into various alterations and modifications without departing from the scope of the appended Claims, and all such alterations and modifications fall within the scope of the present invention. Therefore, the present invention shall be defined by only the claims and their equivalents.

The invention claimed is:

1. A catalytic structure for inducing a predetermined catalytic reaction, the structure comprising:
    a base material configured to be bent by an externally applied force, and
    a catalyst layer formed on the base material,
    wherein the catalyst layer comprises a mixture of a catalytic material and a piezoelectric material, and the catalytic material is configured to be activated when an external energy is applied thereto from an outside,
    wherein at least a part of the catalytic material in the catalyst layer is exposed to the outside, and
    wherein the catalytic structure is configured so that when a force is externally applied to the base material, the piezoelectric material in the catalyst layer generates an electrical potential and the catalytic material in the catalyst layer is activated by the generated electrical potential thereby inducing the catalytic reaction, even at an environment where the external energy is shielded.

2. The catalytic structure according to claim 1, wherein a photocatalyst, an electrochemical catalyst or thermal catalyst is used as the catalytic material.

3. The catalytic structure according to claim 2, wherein at least one of $TiO_2$, ZnO and $MoS_2$ is used as the catalytic material.

4. The catalytic structure according to claim 3, wherein a polymer piezoelectric material is used as the piezoelectric material.

5. The catalytic structure according to claim 4, wherein PVDF-TrFE (polyvinyledenedifluoride-tetrafluoroethylene) is used as the piezoelectric material.

6. The catalytic structure according to claim 1, wherein at least a part of the catalytic material in the catalyst layer is exposed to the outside by a plasma treatment for the catalyst layer.

7. The catalytic structure according to claim 1, wherein the catalyst layer is formed on both surfaces of the base material.

8. A method of manufacturing a catalytic structure for inducing a predetermined catalytic reaction, the method comprising the steps of:
    providing a base material configured to be bent by an externally applied force;
    forming a catalyst layer on the base material, wherein the catalyst layer comprises a mixture of a catalytic material and a piezoelectric material, and the catalytic material is configured to be activated when an external energy is applied thereto from an outside, and
    exposing at least a part of the catalytic material in the catalyst layer to the outside, and
    wherein the catalytic structure is configured so that when a force is externally applied to the base material, the piezoelectric material in the catalyst layer generates an electrical potential and the catalytic material in the catalyst layer is activated by the generated electrical potential thereby inducing the catalytic reaction, even at an environment where the external energy is shielded.

9. The method according to claim 8, wherein a photocatalyst, an electrochemical catalyst or thermal catalyst is used as the catalytic material.

10. The method according to claim 9, wherein at least one of $TiO_2$, ZnO and $MoS_2$ is used as the catalytic material.

11. The method according to claim 10, wherein a polymer piezoelectric material is used as the piezoelectric material.

12. The method according to claim 11, wherein PVDF-TrFE (polyvinyledenedifluoride-tetrafluoroethylene) is used as the piezoelectric material.

13. The method according to claim 12, wherein the catalytic material and the PVDF-TrFE are mixed in an organic solvent and the catalyst layer is formed on the base material by spin coating a mixture solution.

14. The method according to claim 8, wherein at least a part of the catalytic material in the catalyst layer is exposed to the outside by a plasma treatment for the catalyst layer.

15. The method according to claim 8, wherein a ratio of the catalytic material to the piezoelectric material in the catalyst layer increases, contact sites of water molecules or organic matters with the catalyst layer increases.

16. The method according to claim 8, wherein the catalyst layer is formed on both surfaces of the base material.

* * * * *